US006444228B1

(12) United States Patent
Baugh et al.

(10) Patent No.: US 6,444,228 B1
(45) Date of Patent: Sep. 3, 2002

(54) AUTOLOGOUS FIBRIN SEALANT AND METHOD FOR MAKING THE SAME

(75) Inventors: Robert F. Baugh, Parker; Lisa M. Lim, Aurora; Julie S. Johnston, Highlands Ranch; John G. Rivera, Aurora, all of CO (US)

(73) Assignee: Medtronic, Inc., Minneapolis, MN (US)

( * ) Notice: Subject to any disclaimer, the term of this patent is extended or adjusted under 35 U.S.C. 154(b) by 778 days.

(21) Appl. No.: 09/063,338

(22) Filed: Apr. 20, 1998

Related U.S. Application Data

(63) Continuation-in-part of application No. 08/640,278, filed on Apr. 30, 1996, now abandoned.

(51) Int. Cl.$^7$ ............................................... A61K 35/16
(52) U.S. Cl. ....................... 424/530; 424/529; 424/531; 424/532
(58) Field of Search ............................... 424/529, 530, 424/531, 532

(56) References Cited

U.S. PATENT DOCUMENTS

| | | | |
|---|---|---|---|
| 4,627,879 A | | 12/1986 | Rose |
| 5,354,682 A | | 10/1994 | Kingdon et al. |
| 5,391,380 A | * | 2/1995 | Barrow et al. ............... 424/570 |
| 5,510,102 A | * | 4/1996 | Cochrum ................. 424/78.08 |
| 5,585,007 A | * | 12/1996 | Antanavich et al. ........ 210/782 |
| 5,607,694 A | | 3/1997 | Marx |
| 5,643,192 A | * | 7/1997 | Hirsh et al. ..................... 604/4 |
| 5,788,662 A | * | 8/1998 | Antanavich et al. ............ 604/6 |

FOREIGN PATENT DOCUMENTS

| | | |
|---|---|---|
| EP | 0 443 724 | 8/1991 |
| FR | 2 696 095 | 4/1994 |
| WO | WO 97/29792 | 8/1997 |

OTHER PUBLICATIONS

Marieb, E., Human Anatomy and Physiology, 2d Ed., Benjamin/Cummings, California, 1992, pp. 596–596.*
"Simultaneous Occurrence of Human Antibodies Directed against Fibrinogen, Thrombin, and Factor V Following Exposure to Bovine Thrombin: Effects on Blood Coagulation, Protein C Activation and Platelet Function," Vibhuti D. Chouhan, Raul A. De La Cadena, Chandrasekaran Nagaswami, John W. Weisel, Mehdi Kajani, and A. Koneti Rao, Thrombosis and Haemostasis, 77(2):343–9 (1997).
"Severe Bleeding due to Factor V Inhibitor after Repeated Operations Using Fibrin Sealant containing Bovine Thrombin," W. Muntean, W. Zenz, G. Edlinger, and A Beitzke, Thrombosis and Haemostasis, 77:1223 (1997).
Postoperative Bleeding Induced by Topical Bovine Thrombin: Report of Two Cases, Robert J. Christie, MD, Leonthena Carrington, BS, and Barbara Alving, MD, Surgergy, 121(6):708–710 (Jun. 1977).

"Fibrin Sealant: Summary of a Conference on Characteristics and Clinical Uses," B.M. Alving, M.J. Weinstein, J.S. Finlayson, J.E. Menitove, and J.C. Fratantoni, Transfusion, 35:783–790 (1995).
"Inhibitor to Factor V after Exposure to Fibrin Sealant During Cardiac Surgery in a Two–Year–Old Child," W. Muntean, W. Zenz, K. Finging, G. Zobel, and A Beitzke, Acta Paediatr, 83:84–7 (1994).
"Immunization by Bovine Thrombin Used With Fibrin Glue During Cardiovascular Operations," Micheline Berruyer, BS, Jean Amiral, PhD, Patrick Ffrench, MD, Jean Belleville, MD, Olivier Bastien, MD, Jean Clerc,MD, Alain Kassir, MD, Susanne Estanove, MD, and Marc Dechavanne, MD, The Journey of Thoracic and Cardiovascular Surgery, 105(5):892–897 (May 1993).
"An Anaphylactic Reaction to Topical Fibrin Glue," Hiromasa Mitsuhata, MD, Yuji Horiguchi, MD, Kazuhiko Saitoh, MD, Hirokazu Fukuda, MD, Yosihiro Hirabayasi, MD, Hideaki Togashi, MD, and Reiju Shimizu, MD, Anesthesiology, 81(4):1074–1077 (Oct. 1994).
"Anaphylactic Reaction to Topical Bovine Thrombin," David M. Rothenberg, MD, and James N. Moy, MD, Anesthesiology, 78(4):779–782 (Apr. 1993).
"Clinical Significance of Antibodies to Bovine and Human Thrombin and Factor V After Surgical Use of Bovine Thrombin," Samuel I. Rapaport, MD, Ariella Zivelin, M.Sc., Robert A. Minow, MD, Christine S. Hunter, MD, and Kathleen Donnelly, MS, A.J.C.P., 97(1):84–91 (Jan. 1992).
"Development of Antibodies to Thrombin and Factor V With Recurrent Bleeding in a Patient Exposed to Topical Bovine Thrombin," James L. Zehnder, and Lawrence L.K. Leung, Blood, 76(10):2011–1016 (Nov.15, 1990).

(List continued on next page.)

Primary Examiner—Jean C. Witz
(74) Attorney, Agent, or Firm—Steven C. Petersen; Hogan & Hartson, LLP; Sarah S. O'Rourke

(57) ABSTRACT

In general, the present invention relates to a two-phase method for forming an autologous bioadhesive sealant composition or fibrin glue wherein all of the blood components for the bioadhesive sealant are derived from a patient to whom the bioadhesive sealant will be applied. First, a platelet rich plasma and a platelet poor plasma are formed by centrifuging a quantity of anticoagulated whole blood that was previously drawn from the patient. The platelet rich plasma and platelet poor plasma are then divided into two portions. To the first portion, which is used in phase-one, a compound that reverses the effect of the anticoagulant is added, and a clot is allowed to form. The clot is then triturated and the resulting serum, containing autologous thrombin, is collected. The serum obtained from phase-one is then mixed with the second portion of the platelet rich plasma or platelet poor plasma, used in phase-two, to form the bioadhesive sealant of the present invention.

66 Claims, 7 Drawing Sheets

OTHER PUBLICATIONS

"An Anaphylactic Reaction to Fibrin Glue," Leslie Newberg Milde, MD, *Anesth Analg*, 69:684–6 (1989).

"Iatrogenic Immunization with Bovine Thrombin: A Mechanism for Prolonged Thrombin Times after Surgery," Michael J. Flaherty, MD, Ruth Henderson, and Mark H. Wener, MD, *Annuals of Internal Medicine*, 111(8):631–634 (Oct.15, 1989).

"Clinical Application of The Fibrin Adhesive," Suzuki, M., et al., *Otolaryngology*, 56(11)949–953 (1984), Tokyo.

* cited by examiner

AUTOLOGOUS FIBRIN SEALANT AND METHOD FOR MAKING THE SAME

CROSS-REFERENCE TO OTHER APPLICATIONS

This patent application is a continuation-in-part of U.S. patent application Ser. No. 08/640,278, filed Apr. 30, 1996, now abandoned, and entitled Method For Making Autologous Fibrin Sealant.

BACKGROUND OF THE INVENTION

1. Field of the Invention

The present invention relates to autologous bioadhesive sealant compositions, and more particularly to a convenient and practical two-phase method for preparing a bioadhesive sealant specifically from blood components derived from the patient who is to receive the bioadhesive sealant.

2. Description of the State of the Art

When the lining of a blood vessel is damaged, a complex series of events takes place which is designed to prevent blood loss and, ultimately, to restore the integrity of the vessel. Although short-lived vasoconstriction and physical factors such as the pressure of extruded blood on the vessel wall may play some part in haemostasis, the main factors in the haemostatic mechanism are platelets and the blood coagulation system.

Blood coagulation is the result of the complex interaction of a number of protein clotting factors through a cascade, see FIG. 1. In general, damage to the vascular endothelium exposes subendothelial structures which attract platelets and induce them to aggregate reversibly. The protein thrombin, formed during activation of the coagulation pathway generates insoluble crosslinked fibrils of the protein fibrin and causes the platelets to aggregate irreversibly. The resulting platelet-fibrin clot is an effective barrier against loss of blood from the vascular system and also serves as a scaffold for subsequent repair of the lining of the blood vessel.

A bioadhesive sealant or fibrin glue is a relatively new technological advance which duplicates the biological process of the final stage of blood coagulation. Clinical reports document the utility of fibrin glue in a variety of surgical fields, such as, cardiovascular, thoracic, transplantation, head and neck, oral, gastrointestinal, orthopedic, neurosurgical, and plastic surgery. At the time of surgery, the two primary components comprising the fibrin glue, fibrinogen and thrombin, are mixed together to form a clot. The clot adheres to the necessary tissues, bone, or nerve within seconds, but is then slowly reabsorbed by the body in approximately 10 days by fibrinolysis. Important features of fibrin glue is its ability to: (1) achieve haemostasis at vascular anastomoses particularly in areas which are difficult to approach with sutures or where suture placement presents excessive risk; (2) control bleeding from needle holes or arterial tears which cannot be controlled by suturing alone; and (3) obtain haemostasis in heparinized patients or those with coagulopathy. See, Borst, H. G., et al., *J. Thorac. Cardiovasc. Surg.*, 84:548–553 (1982); Walterbusch, G. J., et al., *Thorac. Cardiovasc. Surg.*, 30:234–235 (1982); and Wolner, F. J., et al., *Thorac. Cardiovasc. Surg*, 30:23–237 (1982).

Despite the effectiveness and successful use of fibrin glue by medical practitioners in Europe, neither fibrin glue nor its essential components fibrinogen and thrombin are widely used in the United States. In large part, this stems from the 1978 U.S. Food and Drug Administration ban on the sale of commercially prepared fibrinogen concentrate made from pooled donors because of the risk of transmission of viral infection, in particular the hepatitis-causing viruses such as HBV and HCV (also known as non A, non B hepatitis virus). In addition, the more recent appearance of other lipid-enveloped viruses such as HIV, associated with AIDS, cytomegalovirus (CMV), as well as Epstein-Barr virus, and the herpes simplex viruses in fibrinogen preparations make it unlikely that there will be a change in this policy in the foreseeable future. For similar reasons, human thrombin is also not currently authorized for human use in the United States. Bovine thrombin, which is licensed for human use in the United States is obtained from bovine sources which do not appear to carry significant risks for HIV and hepatitis, although other bovine pathogens, such as bovine spongiform encephalitis, may be present.

There have been a variety of methods developed for preparing fibrin glue. For example, Rose, et al. discloses a method of preparing a cryoprecipitated suspension containing fibrinogen and Factor XIII useful as a precursor in the preparation of a fibrin glue which involves (a) freezing fresh plasma from a single donor such as a human or other animal, e.g. a cow, sheep or pig, which has been screened for blood transmitted diseases, e.g. one or more of syphilis, hepatitis or acquired. immune deficiency syndrome at about 80° C. for at least about 6 hours, preferably for at least about 12 hours; (b) raising the temperature of the frozen plasma, e.g. to between about 0° C. and room temperature, so as to form a supernatant and a cryoprecipitated suspension containing fibrinogen and Factor XIII; and (c) recovering the cryoprecipitated suspension. The fibrin glue is then prepared by applying a defined volume of the cyroprecipitate suspension described above and applying a composition containing a sufficient amount of thrombin, e.g. human, bovine, ovine or porcine thrombin, to the site so as to cause the fibrinogen in the suspension to be converted to the fibrin glue which then solidifies in the form of a gel. See U.S. Pat. No. 4,627,879.

A second technique for preparing fibrin glue is disclosed by Marx in his U.S. Pat. No. 5,607,694. Essentially a cryoprecipitate as discussed previously serves as the source of the fibrinogen component and then Marx adds thrombin and liposomes. A third method discussed by Berruyer, M. et al., entitled "Immunization by bovine thrombin used with fibrin glue during cardiovascular operations," (*J. Thorac. Cardiovasc. Surg.*, 105(5):892–897 (1992)) discloses a fibrin glue prepared by mixing bovine thrombin not only with human coagulant proteins, such as fibrinogen, fibronectin, Factor XIII, and plasminogen, but also with bovine aprotinin and calcium chloride.

The above patents by Rose, et al., and Marx, and the technical paper by Berruyer, et al. each disclose methods for preparing fibrin sealants; however, each of these methods suffer disadvantages associated with the use of bovine thrombin as the activating agent. A serious and life threatening consequence associated with the use of fibrin glues comprising bovine thrombin is that patients have been reported to have a bleeding diathesis after receiving topical bovine thrombin. This complication occurs when patients develop antibodies to the bovine factor V in the relatively impure bovine thrombin preparations. These antibodies cross-react with human factor V, thereby causing a factor V deficiency that can be sufficiently severe to induce bleeding and even death. See, Rapaport, S. I., et al., *Am. J. Clin. Pathol.*, 97:84–91 (1992); Berruyer, M., et al., *J. Thorac. Cardiovasc. Surg.*, 105:892–897 (1993); Zehnder, J., et al., *Blood*, 76(10):2011–2016 (1990); Muntean, W., et al., *Acta Paediatr.*, 83:84–7 (1994); Christine, R. J., et al., *Surgery*, 127:708–710 (1997).

Further disadvantages associated with the methods disclosed by Marx and Rose, et al. are that the cryoprecipitate preparations require a large time and monetary commitment to prepare. Furthermore, great care must be taken to assure the absence of any viral contaminants.

A final disadvantage associated with the methods previously disclosed is that while human thrombin is contemplated for use as an activator, human thrombin is not available for clinical use and there is no evidence that patients will not have an antigenic response to human thrombin. By analogy, recombinant human factor VIII has been shown to produce antigenic responses in hemophiliacs. See, Biasi, R. de., *Thrombosis and Haemostasis*, 71(5):544–547 (1994). Consequently, until more clinical studies are performed on the effect of human recombinant thrombin one cannot merely assume that the use of recombinant human thrombin would obviate the antigenic problems associated with bovine thrombin. A second difficulty with thrombin is that it is autocatalytic, that is, it tends to self destruct making handling and prolonged storage a problem.

There is still a need, therefore, for a convenient and practical method for preparing a bioadhesive sealant composition wherein the resulting bioadhesive sealant poses a zero risk of disease transmission and a zero risk of causing an adverse physiological reaction.

SUMMARY OF THE INVENTION

Accordingly, it is an object of this invention to provide a method for preparing a completely autologous bioadhesive sealant composition.

Another object of the present invention is to provide an autologous bioadhesive sealant composition wherein the risks associated with the use of bovine and with recombinant human thrombin are eliminated.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

To achieve the foregoing and other objects and in accordance with the purposes of the present invention, as embodied and broadly described therein, the method of this invention comprises the formation of an autologous bioadhesive sealant comprising the steps of forming a platelet rich plasma or platelet poor plasma containing an anticoagulant. The platelet rich plasma or platelet poor plasma is then divided into two portions and the first portion is restored so that it can coagulate thus forming a clot. The clot is then triturated and the resulting serum is collected. The bioadhesive sealant composition is then prepared by combining a defined volume of the second portion of platelet rich plasma or platelet poor plasma with a sufficient volume of serum causing the fibrinogen in the second portion of platelet rich plasma or platelet poor plasma to be converted to fibrin which then solidifies in the form of a gel.

BRIEF DESCRIPTION OF THE DRAWINGS

The accompanying drawings, which are incorporated herein and form a part of the specification illustrate preferred embodiments of the present invention, and together with the description, serve to explain the principles of the invention.

In the Drawings

DETAILED DESCRIPTION OF THE PREFERRED EMBODIMENT

Figure 1:
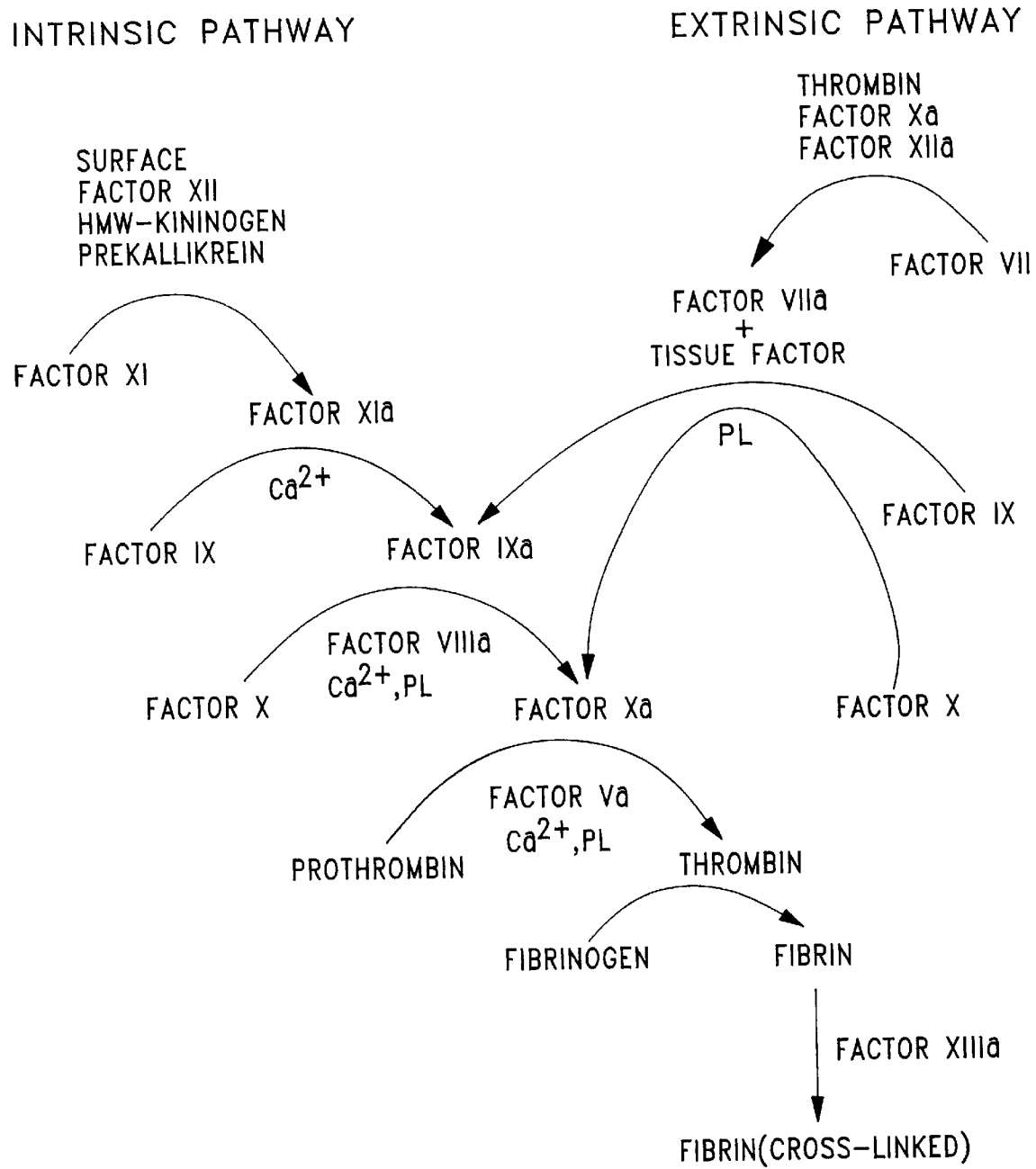
FIG. 1 is a diagrammatic representation of the blood coagulation cascade.
Figure 2A:
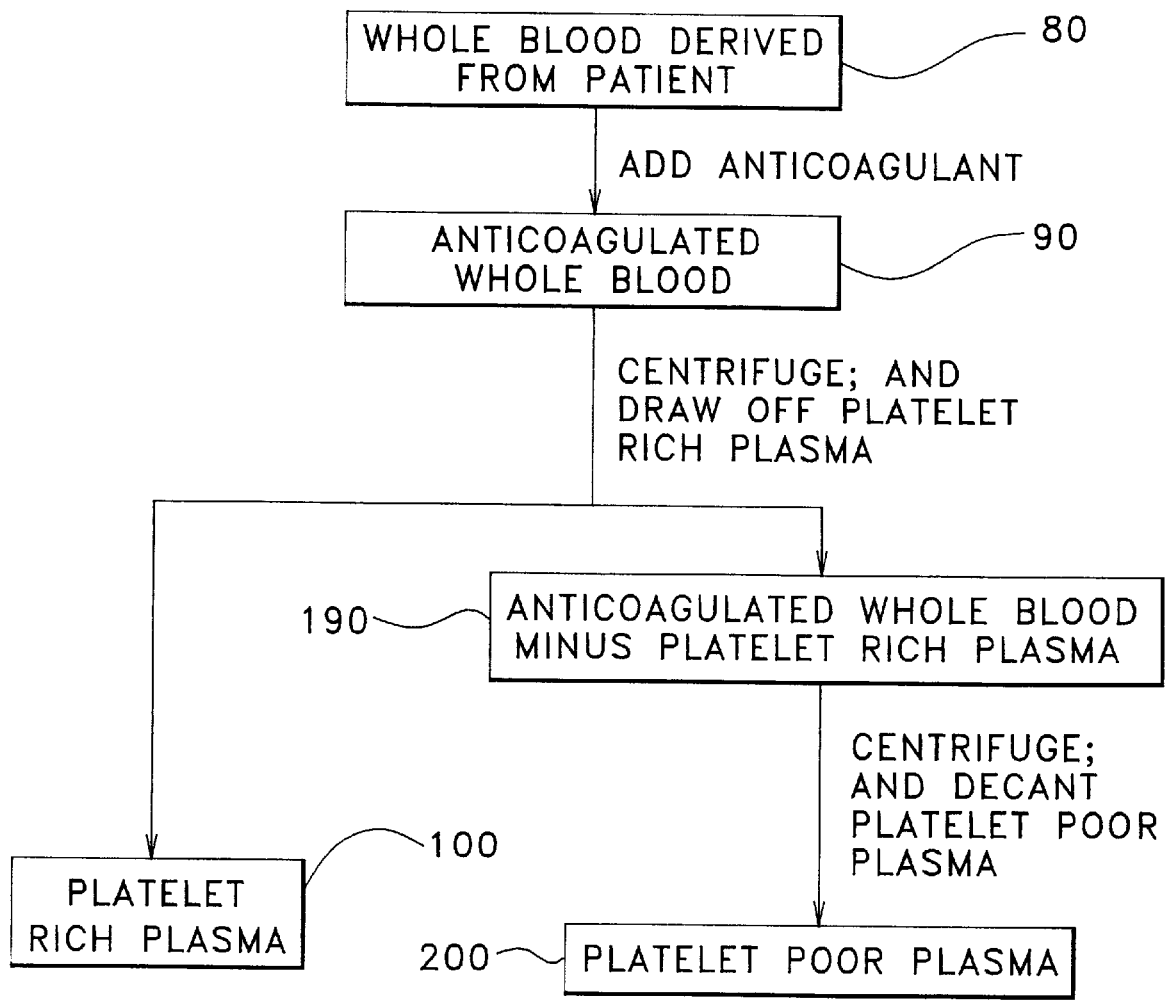
FIG. 2*a* is a flow diagram representing the initial portion of the method of the present invention used to obtain platelet rich plasma and platelet poor plasma.
Figure 2B:
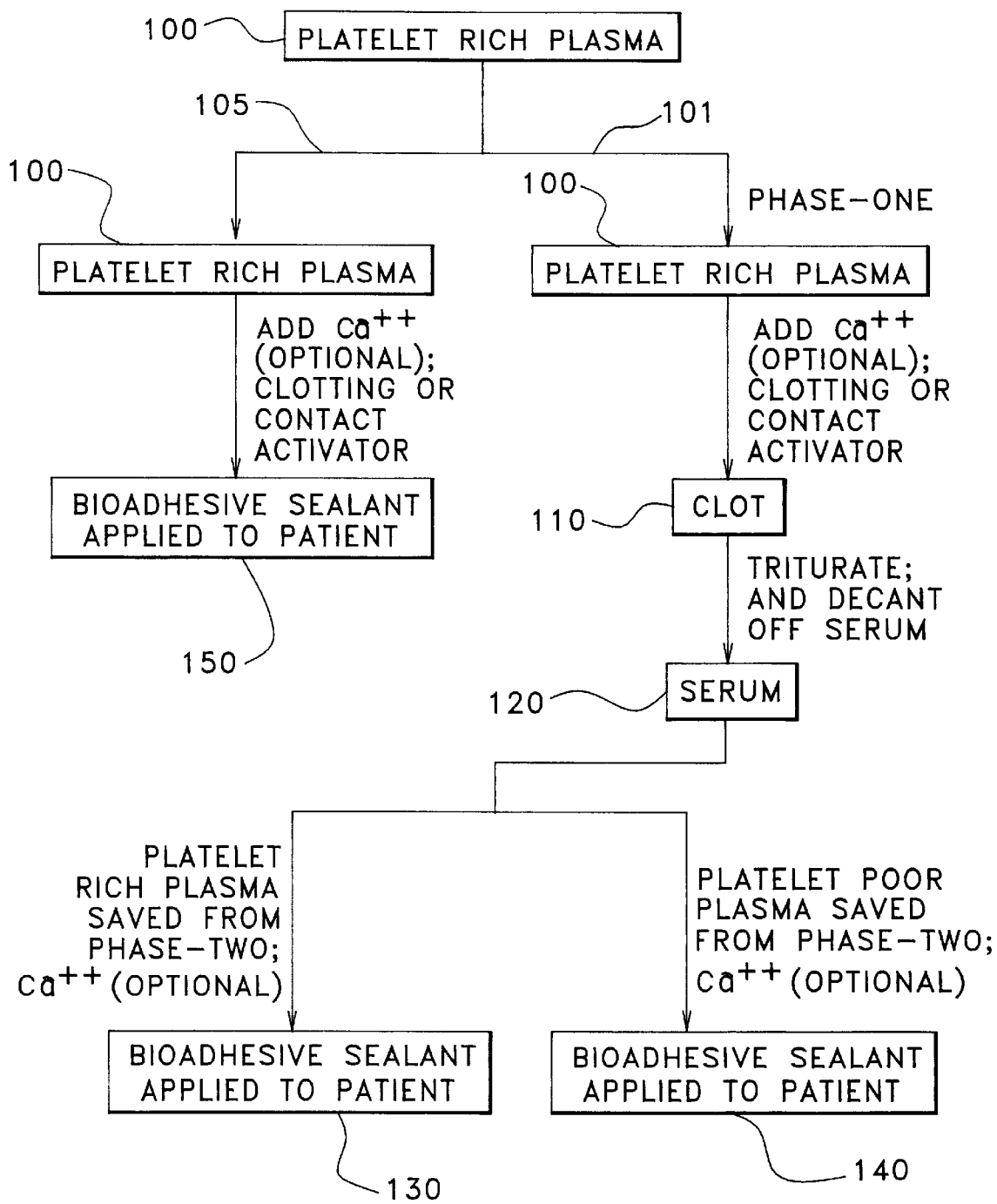
FIG. 2*b* is a flow diagram representing the final portion of the method for preparing the bioadhesive sealant composition of the present invention using platelet rich plasma as a starting material.
Figure 2C:
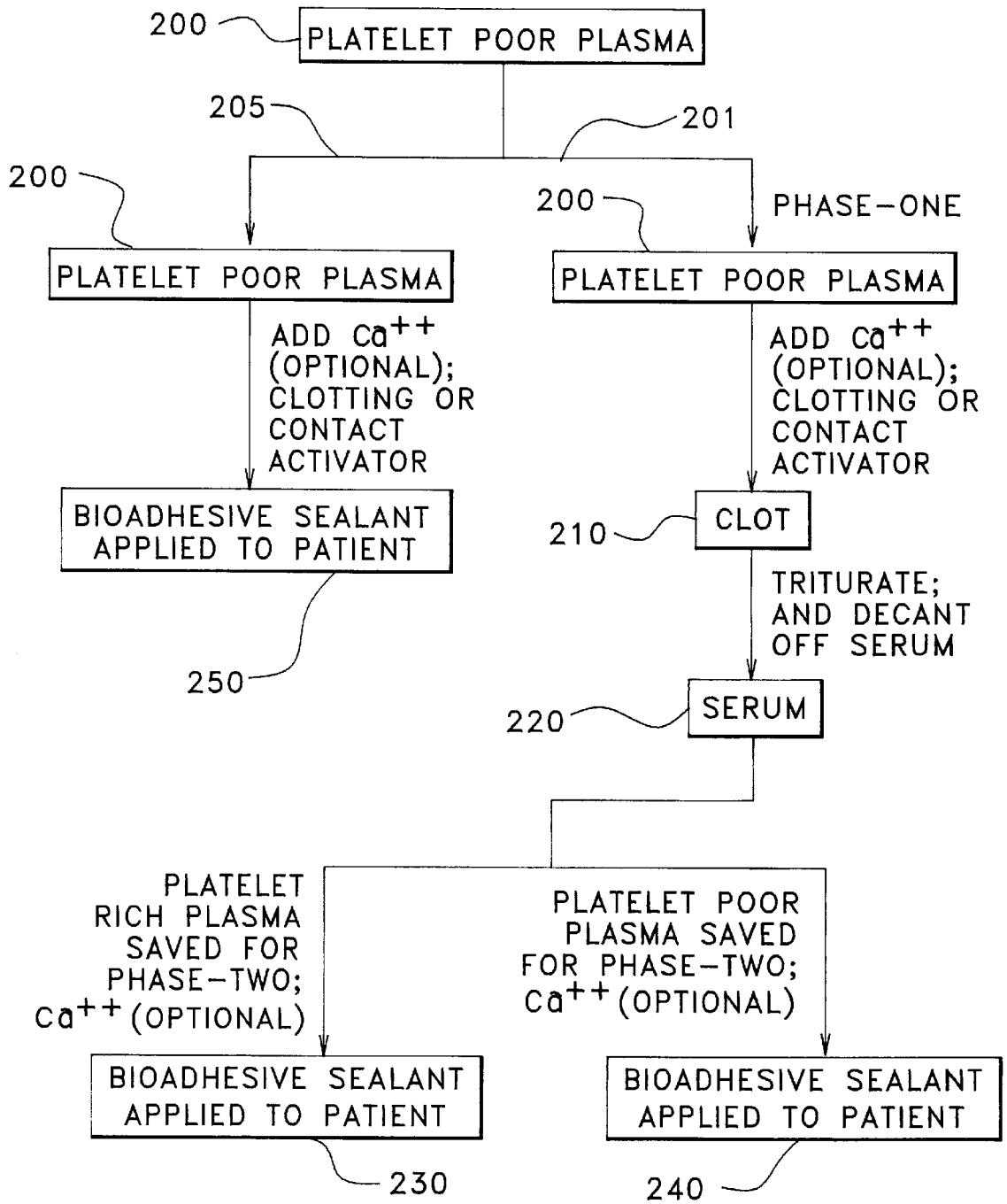
FIG. 2*c* is a flow diagram representing the final portion of the method for preparing the bioadhesive sealant composition of the present invention using platelet poor plasma as a starting material.

In general, the present invention relates to a two-phase method, shown in FIGS. 2*a*, 2*b* and 2*c*, for forming an autologous bioadhesive sealant composition or fibrin glue wherein all of the blood components for the bioadhesive sealant are derived from a patient to whom the bioadhesive sealant will be applied. First, a platelet rich plasma and a platelet poor plasma are formed by centrifuging a quantity of anticoagulated whole blood that was previously drawn from the patient. The platelet rich plasma and platelet poor plasma are then divided into two portions. To the first portion, which is used in phase-one, a compound that reverses the effect of the anticoagulant is added, and a clot is allowed to form. The clot is then triturated and the resulting serum, containing autologous thrombin, is collected. The serum obtained from phase-one is then mixed with the second portion of the platelet rich plasma or platelet poor plasma, used in phase-two, to form the bioadhesive sealant of the present invention.

The method of the present invention for preparing an autologous bioadhesive composition, discussed in further detail below, is represented in the flow diagram depicted in FIGS. 2*a*, 2*b* and 2*c*. The method of the present invention begins by forming anticoagulated whole blood 90 which is achieved by collecting a patient's whole blood 80 in a medium containing an anticoagulation agent, such as sodium citrate (citrate) or heparin. The act of drawing blood initiates clotting reactions, and unless something is done to stop the process, a clot will form. The formation of a clot is a multi-step process and several of these steps require the presence of calcium ions. By removing the calcium ions present in whole blood, as is the effect when the blood is collected in citrate, the blood can be prevented from clotting. To reinitiate the clot-forming process, calcium is added back into the whole blood (recalcification). A calcium chelating agent is a chemical which reacts with the calcium, present in blood, in such a fashion that the calcium can no longer function in blood coagulation. The most common chelating agent is a salt of citric acid (citrate), since it has the fewest side effects on the components of the clotting system. By collecting blood into a medium containing a calcium chelating agent such as citrate, sample collection and further preparations of the citrated sample can be performed over a time period of up to several hours.

Preferably, the whole blood 80 is collected and mixed with a 3.8% solution of sodium citrate (referred to herein as "citrate collection medium") specifically in a 9:1 ratio of blood to citrate collection medium. A 3.8% solution of sodium citrate is prepared by adding 3.8 grams of sodium citrate per 100 ml of water. While a 3.8% sodium citrate collection medium is that which is frequently used to collect and preserve blood, the person skilled in this art will recognize that the ratio of sodium citrate to whole blood could be in the range of about 10.9–12.9% mM/L, final concentration.

The anticoagulated whole blood 90 is next centrifuged at a rate of approximately 20–50 r.c.f.'s (relative centrifugal force) for 10–40 minutes, and preferably in a refrigerated centrifuge at 25 r.c.f.'s for 20 minutes, resulting in the formation of two liquid phases. The top phase is a platelet rich plasma (PRP) 100, and the bottom phase is anticoagulated whole blood minus the platelet rich plasma 190. The platelet rich plasma (PRP) 100 is then gently drawn off and saved in a container.

The remaining anticoagulated whole blood minus the platelet rich plasma phase 190 is further centrifuged at a rate of approximately 3000–4500 r.c.f.'s for 15–30 minutes, and preferably in a refrigerated centrifuge at 3850 r.c.f.'s for 20 minutes. This higher rate of centrifugation results in the red blood cells, white blood cells and platelets being spun out of the anticoagulated whole blood minus the platelet rich plasma phase 190 thereby forming a pellet (not shown) comprising cellular components which is to be discarded. The resulting platelet poor plasma (PPP) 200 is then decanted from the pellet and saved in a container. The containers (not shown) which store the platelet rich plasma 100 and platelet poor plasma 200 may have either wettable surfaces (such as, silica, diatemaceous earth, kaolin, etc.) or non-wettable surfaces (such as plastic, siliconized glass, etc.). Since surfaces play a role in activating blood coagulation, the surface of the container chosen to store either the platelet rich plasma 100 or the platelet poor plasma 200 is dependent on whether clot formation is desired quickly or slowly. Chemical activators, such as kaolin, can also be used to speed up the clotting time; however, their subsequent removal would also be necessary. In the preferred embodiment, a glass tube is the preferred container used to collect the platelet rich plasma 100 and the platelet poor plasma 200.

In the preferred embodiment, according to route 101, the platelet rich plasma 100 is divided into two portions. The first portion is approximately ¼ to ½ of the total volume of platelet rich plasma 100 and is utilized in phase-one to prepare the thrombin, while the second portion of platelet rich plasma 100 is utilized in phase-two. Once the platelet rich plasma 100 and the platelet poor plasma 200 are obtained, the preferred methods to obtain the bioadhesive sealant compositions in an expedited manner, that is, in less than two minutes, are detailed diagrammatically in routes 101 or 201, shown in FIGS. 2b and 2c, respectively and discussed in detail below. If, however, a longer R clotting time, that is, in a range of two to eight minutes, is desirous, the method to obtain the bioadhesive sealant composition of the present invention can proceed along the routes 105 and 205, which are also detailed diagrammatically in FIGS. 2b and 2c, respectively and discussed in detail below.

Phase-one according to the preferred embodiment begins by restoring the clot-forming process. To accomplish this, an agent (restoration agent) capable of reversing the effects of the anticoagulation agent is added back into the first portion of the platelet rich plasma 100. In the presently preferred embodiment of the invention, the reversal of the anticoagulant is accomplished using calcium chloride. However, any substance which is known or found to be functionally equivalent to calcium chloride, such as, calcium gluconate, in restoring the coagulation activity of citrated blood may be used in the practice of the present invention. Thus, although calcium chloride is the presently preferred calcium salt for use in the invention, any calcium salt which functions in a similar manner to calcium chloride may be used in the invention. Similarly, although many blood coagulation reactions are currently believed to require calcium ions as cofactors, any substance which is known or subsequently found to be functionally equivalent to calcium in facilitating these coagulation reactions may be used, either individually or in combination with calcium, in the practice of the present invention. If the anticoagulation agent used was heparin, then heparinase would be used to reverse the effect of the anticoagulation agent. The concentration of the restoration agent used to reverse the anticoagulation will depend in part, upon the concentration of the anticoagulation agent in the platelet rich plasma 100 and the stoichiometry of the chelating and coagulation reactions. However, the concentration of the restoration agent used to reverse the anticoagulation must be sufficient to achieve clot formation.

Upon restoration of the platelet rich plasma 100 as shown in FIG. 2b, a clot 110 will naturally form. The resulting clot 110 is then triturated by high speed centrifugation, or squeezed through a mesh, thus releasing a serum 120 that comprises thrombin. In the preferred embodiment, the serum 120 is then mixed with the second portion of platelet rich plasma (PRP) 100 to form the bioadhesive sealant composition 130 of the present invention in less than two minutes and in quantities sufficient for clinical use.

In an alternative embodiment, serum 120 is mixed with the platelet poor plasma 200 of phase-two thereby forming the autologous bioadhesive sealant composition 140 of the present invention in less than two minutes.

A third embodiment of the present invention, route 105, shown in FIG. 2b, contemplates collecting the original quantity of platelet rich plasma (PRP) 100 derived from the anticoagulated whole blood 90 in a container, having a wettable surface, such as glass. The platelet rich plasma 100 is then recalcified and the bioadhesive sealant composition 150 forms. The desired bioadhesive sealant composition 150 will require approximately two to eight minutes to form as opposed to less than a two minute formation as was described in the preferred embodiment.

In the fourth embodiment depicted diagrammatically by route 201 in FIG. 2c, the platelet poor plasma 200, rather then the platelet rich plasma 100, is divided into two portions, as discussed previously in the preferred embodiment. The first portion, used in phase-one, which is approximately ¼ to ½ the original volume is stored in a container having a wettable surface, then the restoration agent, preferably calcium chloride, is added directly to the platelet poor plasma 200. Surface activation of the restored platelet poor plasma 200 occurs as result of the container's surface and a clot forms. The resulting clot is triturated, as described previously, and the serum 220 is collected. Serum 220 is then mixed with the platelet rich plasma 100 of phase-two thereby forming the autologous bioadhesive sealant composition 230.

In the fifth embodiment, serum 220 is mixed with the platelet poor plasma 200 of phase-two thereby forming the bioadhesive sealant composition 240 in less than two minutes.

The sixth embodiment follows route 205, shown in FIG. 2c wherein the original quantity of platelet poor plasma 200, derived from the anticoagulated whole blood minus platelet rich plasma 190, is collected in a container having a wettable surface, such as glass. The platelet poor plasma 200 is then recalcified and the bioadhesive sealant composition 250 forms.

A seventh embodiment contemplates mixing human recombinant thromboplastin directly with the platelet rich plasma to form a bioadhesive sealant composition (not shown). Alternatively, human recombinant thromboplastin is utilized to generate thrombin in a small aliquot of plasma and then the resulting thromin is combined with the platelet rich plasma to form a bioadhesive sealant. Thromboplastin may be later removed by centrifugation.

The tensile strength of the bioadhesive sealant compositions of the present invention can be effected by the addition of calcium ions. Consequently, if a stronger bioadhesive sealant composition is desired using the methods discussed above and disclosed in routes 101 and 201, in FIGS. 2b and 2c, respectively, more calcium ions may be added at the time the serum is introduced into the platelet rich plasma 100 or the platelet poor plasma 200. Alternatively, if the method of preparing the bioadhesive sealant compositions follows routes 105 and 205, depicted in FIGS. 2b and 2c, respectively, then calcium ions may be introduced directly into the platelet rich plasma 100 or the platelet poor plasma 200 and the bioadhesive sealant compositions 150 and 250, respectively, will form.

As discussed in further detail below, the time period necessary for the formation of the bioadhesive sealant composition of the present invention is dependent on the quantity of serum added. A 1:4, 1:2 and 3:4 ratio of serum to platelet rich plasma or platelet poor plasma results in the formation of the bioadhesive gel composition in approximately 90, 55 and 30 seconds, respectively. Furthermore, due to the fact that thrombin is autocatalytic, it is important that the serum be used within five hours of preparation, preferably within two hours and ideally immediately. Alternatively, the serum can be chilled or frozen indefinitely.

The bioadhesive sealant compositions of this invention may be used for sealing a surgical wound by applying to the wound a suitable amount platelet rich plasma or platelet poor plasma once it has begun to gel. Moreover, due to the fact that the bioadhesive sealant compositions of the present invention have been prepared soley from blood components derived from the patient that is to receive the bioadhesive sealant there is a zero probability of introducing a new blood transmitted disease to the patient. The methods of the present invention may be further modified so that the formed bioadhesive sealant composition functions not only as a haemostatic agent, but also as an adjunct to wound healing and as a matrix for delivery of drugs and proteins with other biologic activities. For example, it is well known that fibrin glue has a great affinity to bind bone fragments which is useful in bone reconstruction, as in plastic surgery or the repair of major bone breaks. Consequently, in keeping with the autologous nature of the bioadhesive sealant composition of the present invention autologous bone from a patient can be ground or made into powder or the like, and mixed into the platelet rich plasma obtained in phase-two of the methods of the present invention. Serum comprising thrombin is then mixed in with the platelet rich plasma and bone fragments in an amount sufficient to allow the resulting gel to be applied to the desired locale where it congeals.

In instances where the desired bioadhesive sealant composition of the present invention is to further function as a delivery device of drugs and proteins with other biologic activities the method of the present invention may be modified as follows. Prior to adding the serum comprising thrombin, obtained in phase-one, to the platelet rich plasma of phase-two a wide variety of drugs and proteins with other biologic activities may be added to the platelet rich plasma of phase-two. Examples of the agents to be added to the platelet rich plasma prior to the addition of the serum include, but are not limited to, analgesic compounds, antibacterial compounds, including bacteriocidal and bacteriostatic compounds, antibiotics (e.g., adriamycin, erythromycin, gentimycin, penicillin, tobramycin), antifungal compounds, anti-inflammatories, antiparasitic compounds, antiviral compounds, enzymes, enzyme inhibitors, glycoproteins, growth factors (e.g. lymphokines, cytokines), hormones, steroids, glucocorticosteroids, immunomodulators, immunoglobulins, minerals, neuroleptics, proteins, peptides, lipoproteins, tumoricidal compounds, tumorstatic compounds, toxins and vitamins (e.g., Vitamin A, Vitamin E, Vitamin B, Vitamin C, Vitamin D, or derivatives thereof). It is also envisioned that selected fragments, portions, derivatives, or analogues of some or all of the above may be used.

A number of different medical apparatuses and testing methods exist for measuring and determining coagulation and coagulation-related activities of blood. These apparatuses and methods can be used to assist in determining the optimal formulation of activator, that is, thrombin, calcium and plasma necessary to form the bioadhesive sealant composition of the present invention. Some of the more successful techniques of evaluating blood clotting and coagulation are the plunger techniques illustrated by U.S. Pat. No. 4,599,219 to Cooper et al., U.S. Pat. No. 4,752,449 to Jackson et al., and U.S. Pat. No. 5,174,961 to Smith, all of which are assigned to the assignee of the present invention, and all of which are incorporated herein by reference.

Automated apparatuses employing the plunger technique for measuring and detecting coagulation and coagulation-related activities generally comprise a plunger sensor cartridge or cartridges and a microprocessor controlled apparatus into which the cartridge is inserted. The apparatus acts upon the cartridge and the blood sample placed therein to induce and detect the coagulation-related event. The cartridge includes a plurality of test cells, each of which is defined by a tube-like member having an upper reaction chamber where a plunger assembly is located and where the analytical test is carried out, and a reagent chamber which contains a reagent or reagents. For an activated clotting time (ACT) test, for example, the reagents include an activation reagent to activate coagulation of the blood. A plug member seals the bottom of a reagent chamber. When the test commences, the contents of the reagent chamber are forced into the reaction chamber to be mixed with the sample of fluid, usually human blood or its components. An actuator, which is a part of the apparatus, lifts the plunger assembly and lowers it, thereby reciprocating the plunger assembly through the pool of fluid in the reaction chamber. The plunger assembly descends by the force of gravity, resisted by a property of the fluid in the reaction chamber, such as its viscosity. When the property of the sample changes in a predetermined manner as a result of the onset or occurrence of a coagulation-related activity, the descent rate of the plunger assembly therethrough is changed. Upon a sufficient change in the descent rate, the coagulation-related activity is detected and indicated by the apparatus.

Figure 3:
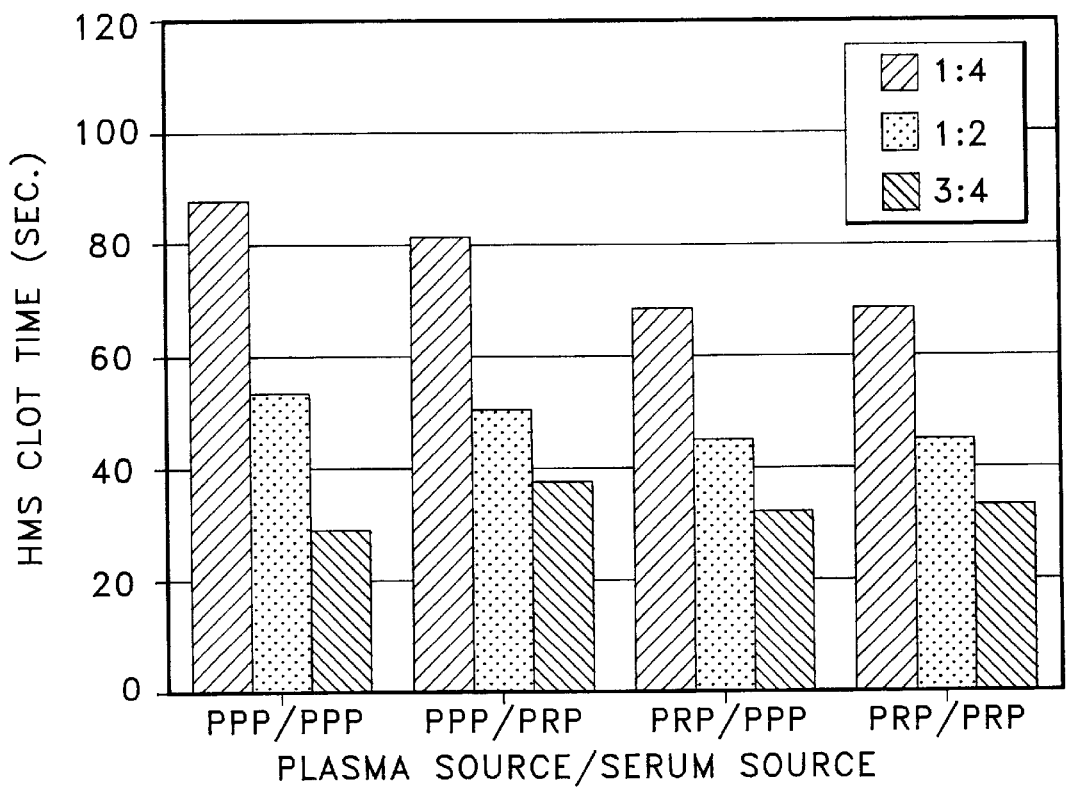
FIG. 3 is a graphic representation of the effect that the serum-to-plasma ratio has on clotting times.
Figure 6:
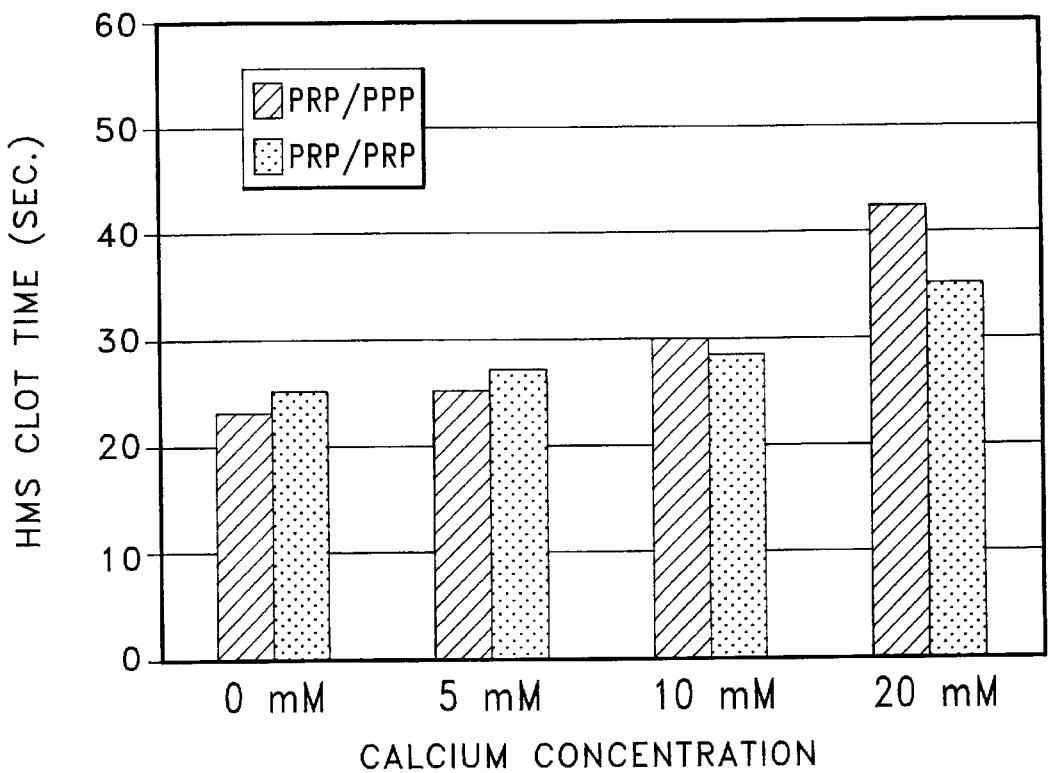
FIG. 6 graphically represents the effect of calcium addition on the clotting times of platelet rich plasma and platelet poor plasma.
Figure 4A:
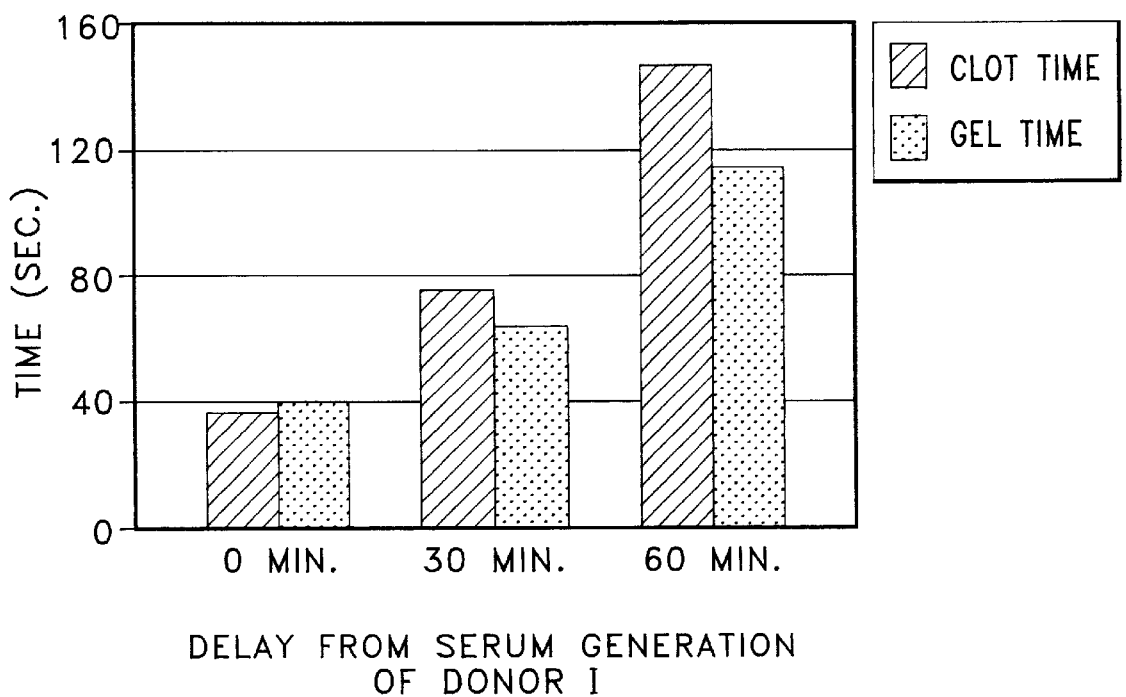
FIG. 4*a* is a graphic representation of the relationship between clotting time and actual gel time using blood drawn from a donor.
Figure 4B:
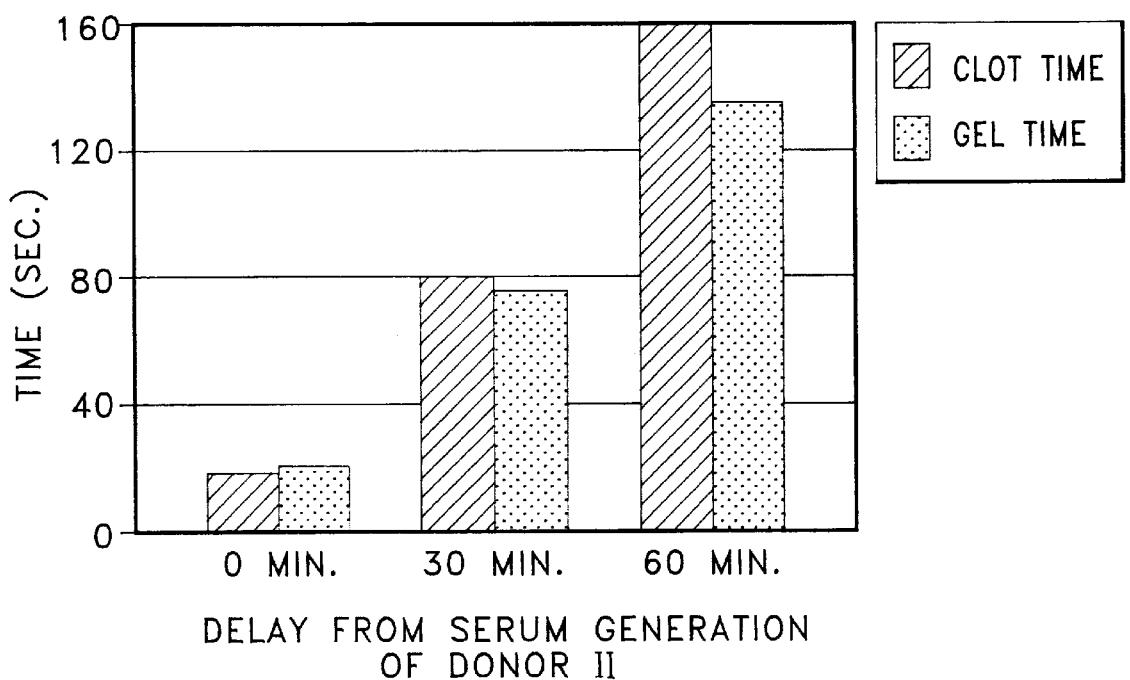
FIG. 4*b* is a graphic representation of the relationship between clotting time and actual gel time using blood drawn from a donor.
Figure 5A:
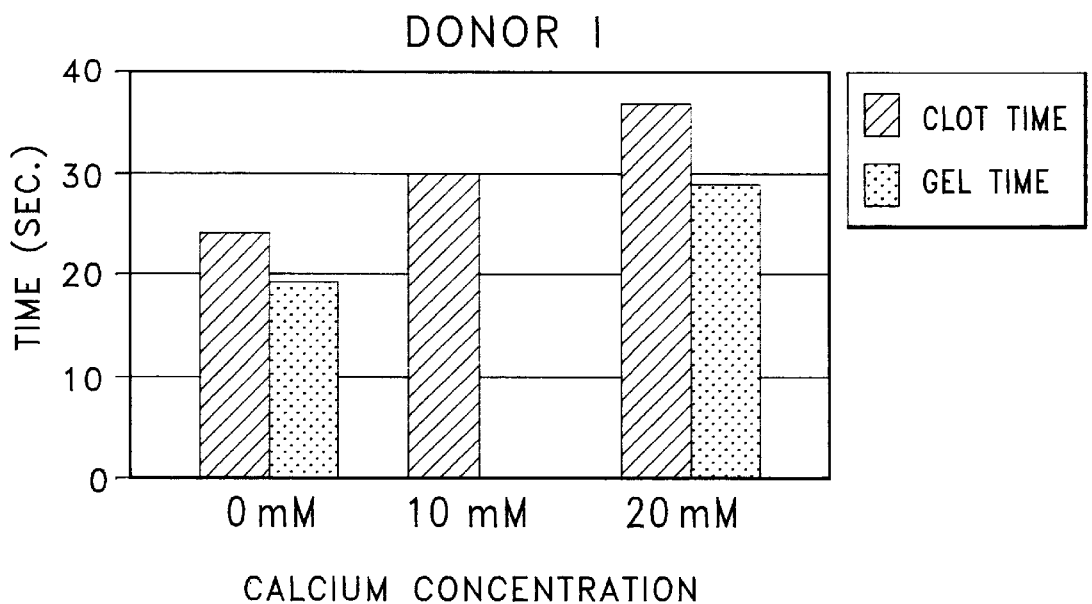
FIG. 5*a* graphically represents the effect of calcium addition on clotting times and gel times using blood drawn from a donor.
Figure 5B:
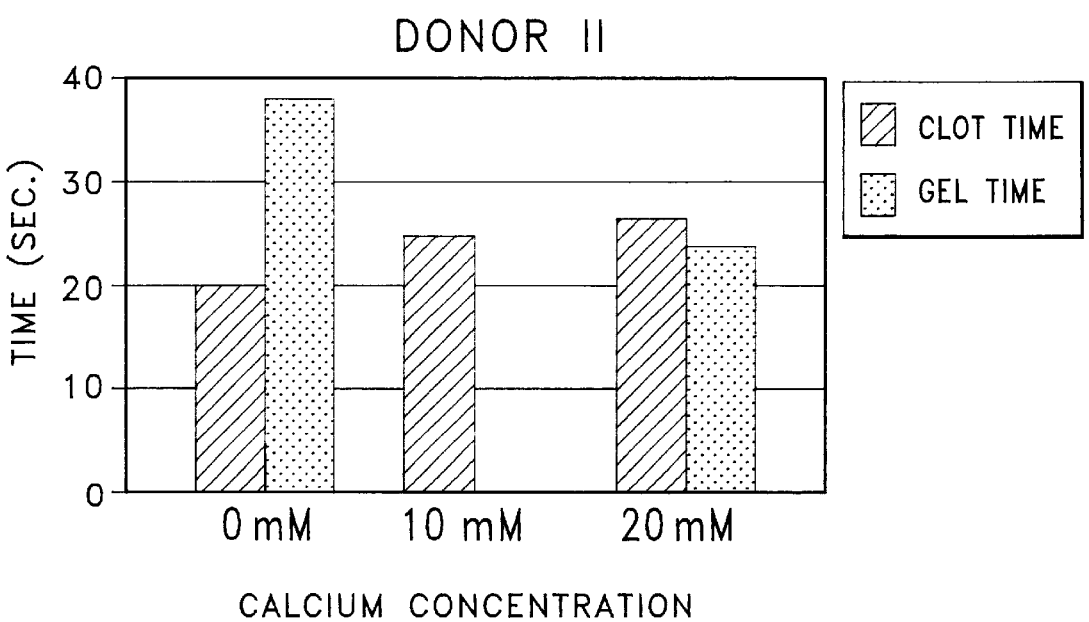
FIG. 5*b* graphically represents the effect of calcium addition on clotting times and gel times using blood drawn from a donor.

Using the methods discussed above, cartridges were assembled with serum obtained from either platelet rich plasma or platelet poor plasma, and $CaCl_2$ in the reagent chambers. Clotting time tests were performed by the automated process with either platelet rich plasma (PRP) or platelet poor plasma (PPP) dispersed into the reaction chambers of the cartridges. In the first experiment, the results of which are represented in FIG. 3, the amount of serum, the type of plasma from which the serum was derived, and the type of plasma the serum was mixed with were tested to determine the shortest clotting times. The ratios of serum to platelet rich plasma or platelet poor plasma that were studied included 1:4, 1:2, and 3:4. In the second set of experiments, the results of which are represented in FIGS. 4a and 4b, the relationship between actual gel time for the bioadhesive sealant composition of the present was compared to the clotting time in the cartridge, wherein there is a 0, 30, or 60 minute delay of adding the serum from its generation. The third set of experiments, the results of which are represented in FIGS. 5a and 5b, studied the effect of calcium addition on actual gel time versus clotting time in the cartridge. The final set of experiments, the results of which are represented in FIG. 6, studied the effect of adding calcium on clotting times.

Although clotting times varied among donors, comparisons of clotting times for individual donors show significant effects of the serum to plasma ratio and the calcium concentration. For all donors, the shortest clotting times occurred for the 3:4 ratio, with clotting times that were 47% shorter than those for the 1:4 ratio. Although the difference in clotting times for the 3:4 ratio and the 1:2 ratio was not statistically significant, the clotting times were consistently shorter using the 3:4 ratio for all donors. These results demonstrate that clotting times may be shortened by increasing the serum to platelet rich plasma ratio. Similarly, clotting times were significantly affected by the amount of calcium added, with the shortest clotting times obtained when no calcium was added, suggesting that the serum contained levels of calcium that were sufficient to recalcify the citrated platelet rich plasma. Preliminary results from the scale-up experiments suggest that experimental clotting times in the cartridges correlate with actual gel times.

The invention is further illustrated by the following non-limited examples. All scientific and technical terms have the meanings as understood by one with ordinary skill in the art. The specific examples which follow illustrate the methods in which the bioadhesive sealant compositions of the present invention may be prepared in a clinical setting and are not to be construed as limiting the invention in sphere or scope. The methods may be adapted to variation in order to produce compositions embraced by this invention but not specifically disclosed. Further, variations of the methods to produce the same compositions in somewhat different fashion will be evident to one skilled in the art.

EXAMPLES

The examples herein are meant to exemplify the various aspects of carrying out the invention and are not intended to limit the invention in any way.

Example 1

Preparation of Bioadhesive Sealant Composition Using Platelet Rich Plasma and Serum 10 cc's of platelet rich plasma is added to a sterile glass tube containing 0.33 cc's of 10% calcium chloride. A stopper is placed in the tube and the contents are gently mixed and the tube is set aside. Gelling of the contents will occur in two to eight minutes. The gel is passed to a dry sterile cup where it is squeezed out 4–6 cc's of the serum, produced therefrom, and 1 cc of air is drawn into a syringe containing 4 cc of platelet rich plasma along with 1 cc of the serum. The bioadhesive sealant composition will gel inside the syringe within approximately two minutes. The gel time may be decreased by increasing the amount of serum added to the platelet rich plasma.

Example 2

10 cc's of whole blood is withdrawn from a patient, placed into a sterile glass tube, and allowed to clot naturally. The clot may be subsequently squeezed or centrifuged to release approximately 4–6 cc's of serum.

An equivalent volume of 10% calcium chloride is then mixed with the serum. 1 cc of this calcified serum is then mixed with 7–8 cc's of platelet rich plasma and 2 cc's of air. The resulting bioadhesive sealant will gel in approximately 1–2 minutes.

Example 3

To a sterile glass syringe containing 0.33 cc's of 10% calcium chloride, 10 cc's of platelet rich plasma is added. The mixture is allowed to rest for 2 to 8 minutes. Once the gel appears to be appropriately viscous, it may be applied to the would site.

The techniques demonstrated in examples 1 and 2 may be simultaneously prepared for (a) an additional source of serum; and (b) to confirm successful coagulation.

The foregoing description is considered as illustrative only of the principles of the invention. Furthermore, since numerous modifications and changes will readily occur to those skilled in the art, it is not desired to limit the invention to the exact construction and processes shown as described above. Accordingly, all suitable modifications and equivalents may be resorted to falling within the scope of the invention as defined by the claims which follow.

What is claimed is:

1. A method of producing an autologous bioadhesive sealant from a single whole blood sample, comprising:
   forming an inactive platelet rich plasma from said whole blood sample;
   dividing said inactive platelet rich plasma into a first and a second portion;
   reactivating said first portion of said inactive platelet rich plasma to form a clot;
   triturating said clot to obtain a serum comprising autologous thrombin from said reactivated first portion; and
   mixing said serum with said second portion of said inactive platelet rich plasma.

2. The method of claim 1, wherein said platelet rich plasma contains sodium citrate.

3. The method of claim 1, wherein said inactivated platelet rich plasma contains heparin.

4. The method of claim 2, wherein said reactivation occurs with the addition of calcium ions.

5. The method of claim 3, wherein reactivation occurs with the addition of heparinase.

6. The method of claim 2, wherein said platelet rich plasma containing sodium citrate is formed by:
collecting said whole blood in a 9:1 ratio of whole blood to 3.8% sodium citrate solution forming a citrated blood mixture; and
centrifuging said citrated blood mixture to form a platelet rich plasma containing sodium citrate.

7. The method of claim 1, wherein said platelet rich plasma is obtained from an individual to whom said autologous bioadhesive sealant is to be applied.

8. A fibrin sealant, comprising:
human recombinant thromboplastin; and
platelet rich plasma.

9. The fibrin sealant of claim 8, wherein said platelet rich plasma is isolated from an individual to whom the fibrin sealant is to be applied.

10. A fibrin sealant, comprising:
platelet rich plasma, wherein said platelet rich plasma is isolated from an individual to whom the fibrin sealant is to be applied; and
thrombin, wherein said thrombin is isolated from a portion of said platelet rich plasma by reactivating said portion of said platelet rich plasma to form a clot and triturating said clot to form a serum containing said thrombin.

11. The method of claim 1, wherein in said triturating comprises squeezing said clot through a mesh to separate said clot from said serum.

12. The method of claim 1, wherein said triturating comprises high speed centrifugation to separate said clot from said serum.

13. The method of claim 1, further comprising adding calcium ions during said mixing of said serum and said second portion of said inactive platelet rich plasma.

14. The method of claim 1, wherein said serum and said second portion of said inactive platelet rich plasma are mixed in a ratio of 1:4 serum to inactive platelet rich plasma.

15. The method of claim 1, wherein said serum and said second portion of said inactive platelet rich plasma are mixed in a ratio of 1:2 serum to inactive platelet rich plasma.

16. The method of claim 1, wherein said serum and said second portion of said inactive platelet rich plasma are mixed in a ratio of 3:4 serum to inactive platelet rich plasma.

17. A method of producing an autologous bioadhesive sealant from a single whole blood sample, comprising:
forming an inactive platelet rich plasma and an inactive platelet poor plasma from said whole blood sample;
reactivating said inactive platelet rich plasma to form a clot;
triturating said clot to obtain a serum comprising autologous thrombin; and
mixing said serum with said inactive platelet poor plasma.

18. The method of claim 17, wherein said inactive platelet rich plasma and said inactivel platelet poor plasma each contains sodium citrate.

19. The method of claim 18, wherein said reactivation occurs with the addition of calcium ions.

20. The method of claim 17, wherein said inactive platelet rich plasma and said inactive platelet poor plasma each contains heparin.

21. The method of claim 20, wherein said reactivation occurs with the addition of heparinase.

22. The method of claim 18, wherein said inactive platelet rich plasma and said inactive platelet poor plasma containing sodium citrate are formed by:
collecting said whole blood in a 9:1 ratio of whole blood to 3.8% sodium citrate solution forming a citrated blood mixture; and
centrifuging said citrated blood mixture to form an inactive platelet rich plasma and an inactive platelet poor plasma each containing sodium citrate.

23. The method of claim 17, wherein said whole blood sample is obtained from an individual to whom said autologous bioadhesive sealant is to be applied.

24. The method of claim 17, wherein in said triturating comprises squeezing said clot through a mesh to separate said clot from said serum.

25. The method of claim 17, wherein said triturating comprises high speed centrifugation to separate said clot from said serums.

26. The method of claim 17, wherein said serum and said inactive platelet poor plasma are mixed in a ratio of 1:4 serum to inactive platelet poor plasma.

27. The method of claim 17, wherein said serum and said inactive platelet poor plasma are mixed in a ratio of 1:2 serum to inactive platelet poor plasma.

28. The method of claim 17, wherein said serum and said inactive platelet poor plasma are mixed in a ratio of 3:4 serum to inactive platelet poor plasma.

29. A method of producing an autologous bioadhesive sealant from a single whole blood sample, comprising:
forming an inactive platelet poor plasma from said whole blood sample;
dividing said inactive platelet poor plasma into a first and a second portion;
reactivating said first portion of said inactive platelet poor plasma to form a clot;
triturating said clot to obtain a serum comprising autologous thrombin; and
mixing said serum with said second portion of said inactive platelet poor plasma.

30. The method of claim 29, wherein said inactive platelet poor plasma contains sodium citrate.

31. The method of claim 30, wherein said reactivation occurs with the addition of calcium ions.

32. The method of claim 29, wherein said inactive platelet poor plasma contains heparin.

33. The method of claim 32, wherein said reactivation occurs with the addition of heparinase.

34. The method of claim 30, wherein said inactive platelet poor plasma containing sodium citrate is formed by:
collecting said whole blood in a 9:1 ratio of whole blood to 3.8% sodium citrate
solution forming a citrated blood mixture; and
centrifuging said citrated blood mixture to form an inactive platelet poor plasma containing sodium citrate.

35. The method of claim 29, wherein said whole blood sample is obtained from an individual to whom said autologous bioadhesive sealant is to be applied.

36. The method of claim 29, wherein in said triturating comprises squeezing said clot through a mesh to separate said clot from said serum.

37. The method of claim 29, wherein said triturating comprises high speed centrifugation to separate said clot from said serum.

38. The method of claim 29, wherein said serum and said second portion of said inactive platelet poor plasma are mixed in a ratio of 1:4 serum to inactive platelet poor plasma.

39. The method of claim 29, wherein said serum and said second portion of said inactive platelet poor plasma are mixed in a ratio of 1:2 serum to inactive platelet poor plasma.

40. The method of claim 29, wherein said serum and said second portion of said inactive platelet poor plasma are mixed in a ratio of 3:4 serum to platelet poor plasma.

41. A method of producing an autologous bioadhesive sealant from a single whole blood sample, comprising:
   forming an inactive platelet rich plasma and an inactive platelet poor sample from said whole blood sample;
   reactivating said inactive platelet poor plasma to form a clot;
   triturating said clot to obtain a serum comprising autologous thrombin; and
   mixing said serum with said inactive platelet rich plasma.

42. The method of claim 41, wherein said inactive platelet rich plasma and said inactive platelet poor plasma each contains sodium citrate.

43. The method of claim 42, wherein said reactivating occurs with the addition of calcium ions.

44. The method of claim 41, wherein said inactive platelet rich plasma and said inactive platelet poor plasma each contains heparin.

45. The method of claim 44, wherein said reactivation occurs with the addition of heparinase.

46. The method of claim 42, wherein said inactive platelet rich plasma and said inactive platelet poor plasma containing sodium citrate are formed by:
   collecting said whole blood in a 9:1 ratio of whole blood to 3.8% sodium citrate solution forming a citrated blood mixture; and
   centrifuging said citrated blood mixture to form an inactive platelet rich plasma and an inactive platelet poor plasma each containing sodium citrate.

47. The method of claim 41, wherein said whole blood sample is obtained from an individual to whom said autologous bioadhesive sealant is to be applied.

48. The method of claim 41, wherein in said triturating comprises squeezing said clot through a mesh to separate said clot from said serum.

49. The method of claim 41, wherein said triturating comprises high speed centrifugation to separate said clot from said serum.

50. The method of claim 41, wherein said serum and said platelet rich plasma are mixed in a ratio of 1:4 serum to platelet rich plasma.

51. The method of claim 41, wherein said serum and said platelet rich plasma are mixed in a ratio of 1:2 serum to platelet rich plasma.

52. The method of claim 41, wherein said serum and said platelet rich plasma are mixed in a ratio of 3:4 serum to platelet rich plasma.

53. A method of producing an autologous bioadhesive sealant from a single whole blood sample, comprising:
   forming an inactive platelet rich plasma from said whole blood sample;
   dividing said inactive platelet rich plasma into a first and a second portion;
   adding human recombinant thromboplastin to said first platelet rich plasma portion to produce thrombin; and
   combining said thrombin with said second portion of said inactive platelet rich plasma.

54. The method of claim 53, wherein said whole blood sample is obtained from an individual to whom said autologous bioadhesive sealant is to be applied.

55. A method for preparing an autologous thrombin composition, said method comprising:
   obtaining inactive plasma from a single donor;
   reactivating said inactive plasma, whereby a clot forms, to produce a serum comprising thrombin; and
   separating said clot from said serum to obtain said autologous thrombin composition.

56. The method of claim 55, wherein said inactive plasma is platelet rich plasma.

57. The method of claim 55, wherein said inactive plasma is platelet poor plasma.

58. The method of claim 55, wherein said inactive plasma contains sodium citrate.

59. The method of claim 58, wherein said reactivating occurs with the addition of calcium ions.

60. The method of claim 55, wherein said inactive plasma contains heparin.

61. The method of claim 60, wherein said reactivating occurs with the addition of heparinase.

62. The method of claim 1, wherein said bioadhesive sealant is produced within two minutes of mixing said serum with said inactive platelet rich plasma.

63. The method of claim 17, wherein said bioadhesive sealant is produced within two minutes of mixing said serum with said inactive platelet poor plasma.

64. The method of claim 29, wherein said bioadhesive sealant is produced within two minutes of mixing said serum with said inactive platelet poor plasma.

65. The method of claim 41, wherein said bioadhesive sealant is produced within two minutes of mixing said serum with said inactive platelet rich plasma.

66. A method of forming an autologous bioadhesive sealant from a single whole blood sample, comprising:
   forming an inactive platelet rich plasma from said whole blood sample;
   dividing said inactive platelet rich plasma into a first and a second portion;
   reactivating said first portion of said inactive platelet rich plasma to form a clot;
   triturating said clot to obtain a serum comprising autologous thrombin; and
   mixing said serum with said second portion of said inactive platelet rich plasma in a ratio of 3:4 serum to platelet rich plasma, wherein said bioadhesive sealant forms in 30 seconds.

* * * * *